United States Patent [19]

Ebine et al.

[11] Patent Number: 5,178,869

[45] Date of Patent: Jan. 12, 1993

[54] LIQUID DENTIFRICE COMPOSITIONS

[75] Inventors: Yoshihiro Ebine, Sakura; Kenji Kaneko, Yokohama; Satoshi Hayashi, Oomiya, all of Japan

[73] Assignee: Lion Corporation, Tokyo, Japan

[21] Appl. No.: 648,877

[22] Filed: Jan. 31, 1991

[30] Foreign Application Priority Data

Jan. 31, 1990 [JP] Japan .................. 2-21867
Jan. 31, 1990 [JP] Japan .................. 2-21868
Jan. 31, 1990 [JP] Japan .................. 2-21869
Jan. 31, 1990 [JP] Japan .................. 2-21870

[51] Int. Cl.$^5$ .............................................. A61K 7/16
[52] U.S. Cl. .................................... 424/401; 424/49; 222/192
[58] Field of Search ................. 424/49, 58; 222/192

[56] References Cited

U.S. PATENT DOCUMENTS

| 3,506,757 | 4/1970 | Salzmann | 424/52 |
| 3,683,065 | 8/1972 | Lavster | 424/57 |
| 3,935,307 | 1/1976 | Aimoto et al. | 424/49 |
| 3,963,832 | 6/1976 | Hashimoto et al. | 424/49 |
| 4,108,978 | 8/1978 | Mazzanobile et al. | 424/49 |
| 4,453,979 | 6/1984 | De Masi et al. | 424/49 |
| 4,456,585 | 6/1984 | Hayes et al. | 424/49 |
| 4,483,848 | 11/1984 | Cox et al. | 424/49 |
| 4,590,065 | 5/1986 | Piechota et al. | 424/49 |
| 4,842,165 | 6/1989 | Van Coney | 222/95 |
| 4,857,303 | 8/1989 | Grollier | 424/54 |

FOREIGN PATENT DOCUMENTS

| 46-36599 | 10/1971 | Japan . |
| 55-15443 | 4/1980 | Japan . |
| 60-75412 | 4/1985 | Japan . |
| 60-75413 | 4/1985 | Japan . |
| 1189751 | 4/1970 | United Kingdom . |
| 1400793 | 7/1975 | United Kingdom . |

Primary Examiner—Shep K. Rose
Attorney, Agent, or Firm—Birch, Stewart, Kolash & Birch

[57] ABSTRACT

Liquid dentifrice compositions having an abrasive uniformly dispersed in aqueous medium have a low viscosity to maintain flow and stability with the lapse of time. The compositions contain 5-40% of silica or similar abrasive and an optional xanthan gum/polyacrylate binder such that they have a visocity of 20-180 poise at 25°C. and a yield value of 1-60 Pa at 25° C.

25 Claims, 1 Drawing Sheet

FIG.1

LIQUID DENTIFRICE COMPOSITIONS

This invention relates to a liquid dentifrice composition having an abrasive uniformly dispersed in aqueous medium and having a sufficient viscosity of 20 to 180 poise at 25° C. to allow for a soft flow.

BACKGROUND OF THE INVENTION

A variety of liquid dentifrices have previously been proposed in the art, such as for example, those disclosed in Japanese Patent Publication Nos. 36599/1970 and 15443/1980, but few liquid dentifrices have been a commercial success. The major problem is low applicability properties in that when liquid dentifrice is applied to a toothbrush, it will quickly soak through the bristles and flow down from the brush. Another problem of prior art liquid dentifrices is their excess flow or extrudability in that in dispensing the liquid dentifrice from a plastic bottle or similar container, an excess of liquid dentifrice is often applied to the toothbrush.

For these and other reasons, toothpastes have enjoyed the most widespread use while some gel dentifrices having a relatively low viscosity (200 to 500 poise) are used as disclosed in Japanese Patent Application Kokai No. 75412/1985 and 75413/1985, for example. Toothpastes and gel dentifrices are less satisfactory with respect to dispersion in the mouth and ease of washing of the toothbrush after use. For instance, most toothpastes are rather difficult to wash away because some deposits are left adhered to the bristles. In this respect, the liquid dentifrice has a hygienic advantage in that the toothbrush is easily washed clean after use. The use of a liquid dentifrice is recommended from the aspects of quick dispersion and easy rinsing of the toothbrush. It is, therefore, desired to solve the poor applicability of liquid dentifrice.

Most prior art liquid dentifrices are free of abrasive. However, it is desirable to blend abrasive in a liquid dentifrice to ensure a stain removing or cleaning power. To this end, the abrasive has to be dispersed in the liquid dentifrice in a stable manner. One prior art approach is to blend xanthane gum for a stable dispersion of the abrasive as disclosed in Japanese Patent Publication No. 36599/1970.

The inventors have found that a liquid dentifrice composition containing an abrasive in an effective amount to provide a cleaning power, say 5 to 40% by weight of the composition, lowers its fluidity with the lapse of time. Although the liquid dentifrice is normally prepared to have a low viscosity, the abrasive blended therein causes the liquid dentifrice to have a lower fluidity with time and eventually lose fluidity after long term storage.

It is, therefore, desired to prevent a liquid dentifrice composition having abrasive blended therein from exhibiting a lowered fluidity with time so that the liquid dentifrice will maintain a soft flow even after long term storage.

SUMMARY OF THE INVENTION

Therefore, an object of the present invention is to provide a novel and improved liquid dentifrice composition having an abrasive dispersed in a low viscous aqueous medium in a stable manner such that the composition maintains adequate applicability without losing fluidity with the lapse of time.

The inventors have found that by adjusting a liquid dentifrice composition having 5 to 40% by weight of an abrasive blended therein to a viscosity of 20 to 180 poise at 25° C. and a yield value of 1 to 60 Pa (pascal) at 25° C., the abrasive is kept stably dispersed for an extended period of time and a lowering of fluidity with time is minimized even with the abrasive content of 5 to 40% by weight. The composition maintains soft flow even after long term storage at elevated temperatures.

This liquid dentifrice is easily applicable to the toothbrush. A mass of liquid dentifrice applied to the toothbrush does not quickly soak through the bristles, but remains on the top of bristles until the user inserts the brush into the mouth for brushing. A desired quantity of liquid dentifrice can be dispensed from a plastic bottle simply by extrusion. In addition, this liquid dentifrice is readily dispersible in the mouth and can be easily washed away from toothbrush bristles.

A change of fluidity with time is more effectively restrained when the abrasive used has a specific surface area of up to 100 m$^2$/g as measured by BET. Silica abrasives are very effective for the purpose. By combining the silica abrasive with a binder in the form of a mixture of xanthane gum and polyacrylate, the stability of yield value of the liquid dentifrice with time is further improved and the dispersion stability and cleaning power are also increased. The present invention is based on these findings.

Therefore, the present invention provides a liquid dentifrice composition comprising an aqueous medium and 5 to 40% by weight of the composition of an abrasive, the composition having a viscosity of 20 to 180 poise at 25° C. and a yield value of 1 to 60 Pa at 25° C.

BRIEF DESCRIPTION OF THE DRAWING

The only figure.

DETAILED DESCRIPTION OF THE INVENTION

In the liquid dentifrice composition of the present invention, an abrasive is uniformly dispersed in a low viscous aqueous medium in a stable manner without settling down. Examples of the abrasive used herein include silica abrasives such as precipitated silica, silica gel, aluminosilicate, and zirconosilicate as well as calcium hydrogen phosphate dihydrate and anhydride, calcium pyrophosphate, calcium carbonate, aluminum hydroxide, alumina, magnesium carbonate, magnesium tertiary phosphate, insoluble sodium metaphosphate, insoluble potassium metaphosphate, titanium oxide, zeolite, aluminum silicate, zirconium silicate, and synthetic resin abrasives alone and mixtures of two or more of them. Preferred among them are silica abrasives for cleaning power and stable dispersion.

The abrasive preferably has a specific surface area of up to 100 m$^2$/g, especially 5 to 30 m$^2$/g as measured by the BET method based on nitrogen adsorption. The use of an abrasive having a specific surface area of up to 100 m$^2$/g is more effective in preventing a change of fluidity with time and maintaining soft flow for an extended period of time. The abrasive may have a particle size approximately equal to that of abrasives used in conventional toothpastes, and most often, a mean particle size of about 1 to 20 μm.

The amount of the abrasive blended is 5 to 40% by weight, preferably 10 to 25% by weight of the total weight of the composition. Less than 5% by weight of the abrasive is too small to provide a cleaning power whereas a composition containing more than 40% by weight of the abrasive loses fluidity.

The liquid dentifrice composition of the present invention having an abrasive dispersed therein is adjusted to a viscosity of 20 to 180 poise, preferably 30 to 70 poise at 25° C. and a yield value of 1 to 60 Pa, preferably 5 to 50 Pa, more preferably 5 to 20 Pa at 25° C. A composition with a viscosity of lower than 20 poise is less easily applicable to the toothbrush whereas a viscosity of higher than 180 poise means a loss of fluidity. A composition with a yield value of lower than 1 Pa is less easily applicable to the toothbrush whereas a yield value of higher than 60 Pa means a loss of fluidity. The viscosity and yield value are measured by the methods which will be described later.

The applicability to toothbrush and flow in container as a function of viscosity and yield value are shown below together with the overall evaluation of these factors.

TABLE 1

| | Applicability to toothbrush | | |
| --- | --- | --- | --- |
| | Viscosity (poise) | | |
| Yield value | <20 | 20–180 | >180 |
| <1 Pa | Poor | Fair | Good |
| 1–60 Pa | Poor | Exc. | Good |
| >60 Pa | Fair | Good | Good |

TABLE 2

| | Flow in container | | |
| --- | --- | --- | --- |
| | Viscosity (poise) | | |
| Yield value | <20 | 20–180 | >180 |
| <1 Pa | Good | Good | Fair |
| 1–60 Pa | Good | Exc. | Poor |
| >60 Pa | Poor | Poor | Poor |

TABLE 3

| | Overall evaluation on use | | |
| --- | --- | --- | --- |
| | Viscosity (poise) | | |
| Yield value | <20 | 20–180 | >180 |
| <1 Pa | Poor | Fair | Fair |
| 1–60 Pa | Poor | Exc. | Poor |
| >60 Pa | Poor | Poor | Poor |

Liquid dentifrice compositions having viscosity and yield values in the above-specified ranges may be obtained by properly selecting the type and amount of ingredients blended therein, especially the type and amount of binder and humectant.

Examples of the binder include binders commonly used in conventional dentifrices, for example, cellulose derivatives such as carboxymethyl cellulose alkali metal salts, methyl cellulose, hydroxyethyl cellulose, and sodium carboxymethylhydroxyethyl cellulose; alginates such as alkali metal alginates (e.g. sodium alginate) and propylene glycol alginate; carrageenan; gums such as xanthan gum, tragacanth gum, karaya gum, and gum arabic; synthetic binders such as polyvinyl alcohol, sodium polyacrylate, and polyvinyl pyrrolidone; and inorganic binders such as aluminum silica gel and Laponite ®. The binders may be used alone or in admixture of two or more. The binder is blended in an effective amount to achieve the viscosity and yield value in the specific ranges, often an amount of 0.05 to 2% by weight, most often 0.1 to 2% by weight of the total weight of the composition.

The choice of the binder is important for achieving the purposes of the invention. The preferred binder is a mixture of xanthan gum and a polyacrylic acid salt such as sodium polyacrylate because this binder mixture is more effective for preventing a change of the liquid dentifrice composition with time, especially a change in yield value with time. Particularly when this binder mixture is combined with a silica abrasive, outstanding stability with time is expectable as well as improved dispersion stability and cleaning power as compared with the use of other abrasives. The use of the binder mixture of xanthan gum and polyacrylate is also effective for improving stringiness. With regard to the effect of binders on the stringiness of toothpaste, various reports were made in the art, but none of the proposals related to the stringiness of low viscous liquid dentifrices like the present invention. The stringiness of low viscous liquid dentifrices was left unsolved. The inventors have found that stringiness can be improved by using a binder mixture of xanthane gum and polyacrylate.

For the binder mixture to be more effective, xanthane gum and polyacrylate are mixed in a weight ratio of 3:1 to 1:5, especially 3:2 to 1:2. The binder mixture may be blended in the composition in the above-mentioned amount, preferably 0.1 to 1% by weight, more preferably 0.1 to 0.5% weight, most preferably 0.3 to 0.5% by weight of the total weight of the composition.

Examples of the humectant include well-known humectants, for example, glycerine, sorbitol, propylene glycol, ethylene glycol, 1,3-butylene glycol, polyethylene glycol, polypropylene glycol, xylitol, maltitol, lactitol, etc. alone and mixtures thereof. The humectant is blended in an effective amount to achieve the viscosity and yield value in the specific ranges, often an amount of 10 to 80% by weight, most often 20 to 60% by weight of the total weight of the composition.

In addition to the above-mentioned ingredients, the composition of the invention may contain anionic, nonionic and ampholytic surface active agents, sweeteners, flavors, coloring agents, preservatives, pharmaceutical agents, and other suitable ingredients. The composition may be prepared by dispersing the ingredients in water.

Examples of the anionic surface active agent include sodium alkyl sulfates such as sodium laurylsulfate and sodium myristylsulfate; sodium N-acylsarcosinates such as sodium N-lauroylsarcosinate and sodium N-myristoylsarcosinate; sodium dodecylbenzenesulfonate; sodium hydrogenated coconut fatty acid monoglyceride monosulfate; sodium laurylsulfoacetate; N-acylglutaminates such as sodium N-palmitoylglutaminate; sodium N-methyl-N-acyltaurine, sodium N-methyl-N-acylalanine, sodium α-olefinsulfonate, sodium dioctylsulfosuccinate, etc.

Examples of the nonionic surface active agent include saccharide fatty acid esters such as sucrose fatty acid esters, maltose fatty acid esters, and lactose fatty acid esters; saccharide alcohol fatty acid esters such as maltitol fatty acid esters and lactitol fatty acid esters; fatty acid polyglycerin esters such as decaglyceryl monolaurate and diglyceryl monostearate; polyoxyethylene sorbitan fatty acid esters such as polyoxyethylene sorbitan monolaurate and polyoxyethylene sorbitan monostearate; polyoxyethylene fatty acid esters such as polyoxyethylene hardened castor oil; fatty acid mono- or diethanol amides such as lauroyl mono- or diethanol amide and myristoyl mono or diethanol amide; sorbitan fatty acid esters, fatty acid monoglycerides, polyoxyethylene higher alcohol ethers, polyoxyethylene polyoxypropylene copolymers, polyoxyethylene polyoxypropylene fatty acid esters, etc.

Examples of the ampholytic surface active agent include N-alkyldiaminoethylglycines such as N-lauryldiaminoethylglycine and N-myristyldiaminoethylglycine; N-alkyl-N-carboxymethylammonium betaine, sodium 2-alkyl-1-hydroxyethylimidazoline betaine, etc.

These surface active agents may be used alone or in admixture of two or more and generally in amounts of about 0.01 to 5% by weight, preferably about 0.05 to 3% by weight of the total weight of the composition.

Examples of the flavor include menthol, anethol, carvone, eugenol, limonene, ocimene, n-decyl alcohol, citronellol, α-terpineol, methyl salicylate, methyl acetate, citronellyl acetate, cinneol, linalool, ethyl linalool, vanillin, thymol, spearmint oil, peppermint oil, lemon oil, orange oil, sage oil, rosemary oil, cinnamon oil, piment oil, cinnamon leaf oil, perilla oil, wintergreen oil, clove oil, eucalyptus oil, etc. alone and mixtures thereof. The flavor is generally added in an amount of 0 to about 10% by weight, preferably about 0.5 to about 5% by weight of the total weight of the composition.

Examples of the sweetener include saccharin sodium, stevioside, neohesperidyl dihydrochalcone, glycyrrhizin, perillartine, somatin, aspartylphenylalanine methyl ester, p-methoxycinnamic aldehyde, etc. The sweetener is generally added in an amount of 0 to about 1% by weight, preferably about 0.01 to about 0.5% by weight of the total weight of the composition.

Examples of the pharmaceutical agent include cationic bactericides such as chlorohexidine, benzethonium chloride, benzalkonium chloride, cetylpyridinium chloride, and decalinium chloride; enzymes such as dextranase, mutase, lysozyme, amylase, protease, lytic enzyme, and superoxide dismutase; alkali metal monofluorophosphates such as sodium monofluorophosphate and potassium monofluorophosphate; fluorides such as sodium fluoride and stannous fluoride; tranexamic acid, ε-aminocaproic acid, aluminum chlorohydroxyallantoin, dihydrocholestanol, glycyrrhetinic acids, bisabolol, glycerophosphate, chlorophyll, sodium chloride, water-soluble inorganic phosphoric acid compounds, aluminum lactate, zinc chloride, strontium chloride, etc., alone and mixtures thereof.

The preservatives include sodium benzoate, methyl para-hydroxybenzoate, ethyl para-hydroxybenzoate, propyl para-hydroxybenzoate, butyl para-hydroxybenzoate, etc.

The liquid dentifrice composition is generally at pH 4 to 11, preferably at pH 6 to 9.

The liquid dentifrice composition of the invention is transparent when a silica abrasive and an aqueous medium have an approximately equal index of refraction.

Figure 1:
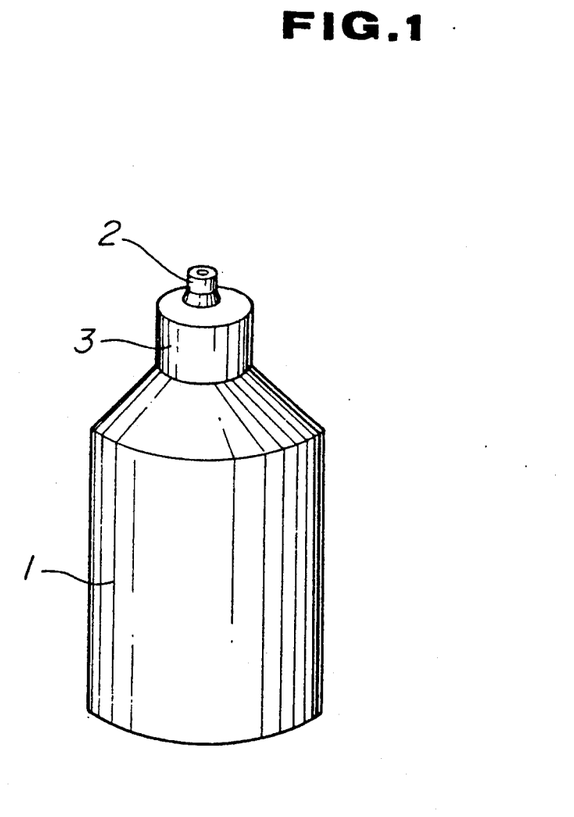
FIG. 1 is a perspective view of a container for receiving a liquid dentifrice composition according to the invention.

The container for receiving the liquid dentifrice composition of the invention is not particularly limited although plastic bottles of the squeeze and pump dispenser types are preferred. Aerosol containers may also be used. One exemplary container for accommodating the liquid dentifrice composition of the invention is shown in FIG. 1. The container includes a container body or housing 1 defining an interior to be filled with the liquid and a mouth piece 3 having a nozzle 2 defining a narrow flowpath through which the liquid passes. The nozzle 2 defines a slit or orifice having a diameter of 0.2 to 8 mm and its flowpath has a transverse cross sectional area of up to 1/30 of the transverse cross sectional area of the housing interior. The liquid can be dispensed in an appropriate necessary volume from such a container without any inconvenience of the liquid flooding out or being blocked.

The liquid dentifrice composition of the invention which has an abrasive dispersed in an aqueous medium in a stable manner is substantially free of a change of flow with time so that it may flow softly even after long-term storage in a container, ensuring easy dispensing from the container. Also it is easily applicable to the toothbrush. It features easy and convenient use.

EXAMPLE

Examples are given below together with comparative examples by way of illustration and not by way of limitation.

In the examples, viscosity, yield value, toothbrush soaking time, flow, dispersion stability, cleaning power, stringiness, and index of refraction were evaluated by the following tests.

(1) Viscosity

Viscometer: BH type viscometer (manufactured by Tokyo Keiki Mfg. K.K.)
Rotor Nos. 4 to 7
Rotation: 20 r.p.m.
Temperature: 25° C.

(2) Yield Value

Tester: HAAKE viscometer
Control unit: RV12 and PG142
Sensor system: MV1 or SV1
Temperature: 25° C.
Rotation: 0 to 128 r.p.m.

The shear stress at which a shear rate vs. shear stress curve deviated from a straight line extending from the origin was measured. A sample was measured both in fresh state (as prepared) and after shelf storage at 40° C. for one month.

(3) Toothbrush Soaking Time

A plastic bottle having a nozzle orifice of 4 mm in diameter was filled with a sample. A 1-gram portion of the sample was extruded on top of the bristle zone of a toothbrush. The time taken until the sample reached the block head was measured.

The toothbrush used had the following specifications.
Bristle zone: 8.8 mm × 26.8 mm (transverse x longitudinal)
Tuft hole: a row of 3 holes plus nine rows of 4 holes, total 39 holes
Number of bristles: 20 bristles/hole
Bristle length: 10.5 mm As a matter of daily practice, ordinary person takes a time of 3 to 12 seconds from application of dentifrice to the toothbrush until insertion into the mouth (a result of 33 persons). On this basis, a sample requiring a time of less than 20 seconds until soaking to the block head was evaluated poor in applicability and a sample requiring a time of 20 seconds or more was evaluated good in applicability.

(4) Flow

A sample in a 80-ml plastic bottle was allowed to stand for one month at 50° C. and then one day at room temperature. Thereafter, the bottle was inclined to evaluate the flow of the sample according to the following criterion.

Rating
5: quick flow
4: flow
3: somewhat slow flow
2: slow flow
1: no flow (5) Dispersion Stability A 80-ml plastic bottle was filled with a sample and maintained in a constant temperature bath at 40° C. for one month. Phase separation was visually observed according to the following criterion.

Rating
OK: No change in appearance
NO: Abrasive settled or syneresis occurred (6) Cleaning Power A solution of tobacco tar and nicotine was uniformly coated to tiles and heated to dryness. Each of the stained tiles was set in a brushing vessel, which was charged with a sample liquid prepared by uniformly dispersing 10 grams of the dentifrice in 15 grams of 60% glycerin solution containing 1% sodium carboxymethyl cellulose. Under a load of 200 grams, the tile was brushed 3,000 times. At the end of brushing, the tile was visually examined for the removal of tar. The rating is an average of three runs. The cleaning power was evaluated according to the following criterion.

| Rating | Tar removal |
| --- | --- |
| OK: | ≧30% |
| Fair: | 20–29% |
| NO: | ≦19% |

(7) Stringiness

Tester: RHEO Meter CR-200D (Sun Scientific Co.)
Plunger: 25 mm × 12 mm (diameter × height)
Speed: 300 mm/min.

The plunger was immersed in a sample up to its top and drawn down at the speed. The length of the resulting string was measured and rated according to the following criterion.

| Rating | |
| --- | --- |
| 3: | <20 mm (passed) |
| 2: | 20–30 mm (passed) |
| 1: | ≧30 mm (rejected) |

(8) Index of Refraction

Tester: Refractometer (Elmer Optical Works Ltd.)
Temperature: 25° C.

(9) Overall Evaluation

Those samples which met all the factors of viscosity, yield value, toothbrush soaking time, flow, dispersion stability, cleaning power, and stringiness passed the test and were rated "Passed". Those samples which were excellent among the passed samples were rated "Exc.Passed". Those samples which did not all the factors were rated "Rejected".

EXAMPLE 1

A liquid dentifrice of the following composition was prepared in a conventional manner and examined for the factors.

| Ingredients | % by weight |
| --- | --- |
| Calcium hydrogen phosphate (specific surface area 6 m$^2$/g) | 25 |
| Xanthan gum | 0.4 |
| Sodium polyacrylate | 0.4 |
| Propylene glycol | 2 |
| Glycerin | 35 |
| Saccharin sodium | 0.1 |
| Flavor | 1.0 |
| Allantoin | 0.02 |
| Dipotassium glycyrrhizinate | 0.01 |
| Sodium laurylsulfate | 1.5 |
| Sodium benzoate | 0.5 |
| Pure water | balance |
| | 100.0% |

| | |
| --- | --- |
| Viscosity | 52 poise |
| Yield value, fresh | 12 Pa |
| after @40° C./1 mth. | 12.5 Pa |
| Brush soaking time | 90 sec. |
| Flow | 5 |
| Dispersion stability | OK |
| Cleaning power | OK |
| Stringiness | 2 |
| Overall evaluation | Passed |

EXAMPLE 2

A liquid dentifrice of the following composition was prepared in a conventional manner and examined for the factors.

| Ingredients | % by weight |
| --- | --- |
| Aluminum hydroxide (specific surface area 3.3 m$^2$/g) | 25 |
| Xanthan gum | 0.35 |
| Sodium polyacrylate | 0.35 |
| Propylene glycol | 2 |
| Glycerin | 35 |
| Saccharin sodium | 0.1 |
| Flavor | 1.0 |
| Tranexamic acid | 0.05 |
| Tocopherol | 0.05 |
| Sodium laurylsulfate | 1.5 |
| Propyl p-hydroxybenzoate | 0.02 |
| Pure water | balance |
| | 100.0% |

| | |
| --- | --- |
| Viscosity | 50 poise |
| Yield value, fresh | 8 Pa |
| after @40° C./1 mth. | 8.3 Pa |
| Brush soaking time | 70 sec. |
| Flow | 5 |
| Dispersion stability | OK |
| Cleaning power | OK |
| Stringiness | 2 |
| Overall evaluation | Passed |

EXAMPLE 3

A liquid dentifrice of the following composition was prepared in a conventional manner and examined for the factors.

| Ingredients | % by weight |
| --- | --- |
| Zirconosilicate (specific surface area 20 m$^2$/g) | 20 |
| Sodium carboxymethyl cellulose | 0.4 |

| | |
|---|---|
| Propylene glycol | 2 |
| Sorbitol | 35 |
| Glycerin | 8.5 |
| Saccharin sodium | 0.1 |
| Flavor | 1.0 |
| Coloring agent (Brilliant Blue) | 0.001 |
| Sodium laurylsulfate | 1.5 |
| Butyl p-hydroxybenzoate | 0.01 |
| Pure water | balance |
| | 100.0% |
| Viscosity | 58 poise |
| Yield value, fresh | 29 Pa |
| after @40° C./1 mth. | 33 Pa |
| Brush soaking time | 77 sec. |
| Flow | 4 |
| Dispersion stability | OK |
| Cleaning power | OK |
| Stringiness | 2 |
| Index of refraction | 1.44 |
| Overall evaluation | Passed |

EXAMPLE 4

A liquid dentifrice of the following composition was prepared in a conventional manner and examined for the factors.

| Ingredients | % by weight |
|---|---|
| Aluminosilicate | 10 |
| (specific surface area 80 m$^2$/g) | |
| Xanthan gum | 0.3 |
| Sodium polyacrylate | 0.5 |
| Propylene glycol | 3 |
| Sorbitol | 20 |
| Glycerin | 40 |
| Saccharin sodium | 0.1 |
| Flavor | 1.0 |
| Cetyl pyridinium chloride | 0.02 |
| Coloring agent (Brilliant Blue) | 0.001 |
| Sodium laurylsulfate | 2.0 |
| Methyl p-hydroxybenzoate | 0.02 |
| Pure water | balance |
| | 100.0% |
| Viscosity | 95 poise |
| Yield value, fresh | 15 Pa |
| after @40° C./1 mth. | 16 Pa |
| Brush soaking time | 250 sec. |
| Flow | 4 |
| Dispersion stability | OK |
| Cleaning power | OK |
| Stringiness | 3 |
| Index of refraction | 1.45 |
| Overall evaluation | Passed |

EXAMPLE 5

A liquid dentifrice of the following composition was prepared in a conventional manner and examined for the factors.

| Ingredients | % by weight |
|---|---|
| Precipitated silica | 20 |
| (specific surface area 40 m$^2$/g) | |
| Carrageenan | 0.5 |
| Propylene glycol | 2 |
| Sorbitol | 35 |
| Glycerin | 8.5 |
| Saccharin sodium | 0.1 |
| Flavor | 1.0 |
| Sodium tripolyphosphate | 1.0 |
| Coloring agent (Brilliant Blue) | 0.001 |
| Sodium laurylsulfate | 1.5 |
| Ethyl p-hydroxybenzoate | 0.02 |
| Pure water | balance |
| | 100.0% |
| Viscosity | 83 poise |
| Yield value, fresh | 50 Pa |
| after @40° C./1 mth. | 51.5 Pa |
| Brush soaking time | 34 sec. |
| Flow | 4 |
| Dispersion stability | OK |
| Cleaning power | OK |
| Stringiness | 2 |
| Index of refraction | 1.44 |
| Overall evaluation | Passed |

EXAMPLE 6

A liquid dentifrice of the following composition was prepared in a conventional manner and examined for the factors.

| Ingredients | % by weight |
|---|---|
| Calcium hydrogen phosphate | 20 |
| (specific surface area 6 m$^2$/g) | |
| Xanthan gum | 0.2 |
| Carrageenan | 0.2 |
| Propylene glycol | 2 |
| Sorbitol | 30 |
| Glycerin | 20 |
| Saccharin sodium | 0.1 |
| Flavor | 1.0 |
| Dextranase (1,200,000 U/g) | 0.2 |
| Mutanase (20,000 U/g) | 0.2 |
| Sodium laurylsulfate | 1.5 |
| Sodium p-hydroxybenzoate | 0.5 |
| Pure water | balance |
| | 100.0% |
| Viscosity | 45 poise |
| Yield value, fresh | 5.5 Pa |
| after @40° C./1 mth. | 5.7 Pa |
| Brush soaking time | 120 sec. |
| Flow | 5 |
| Dispersion stability | OK |
| Cleaning power | OK |
| Stringiness | 2 |
| Overall evaluation | Passed |

EXAMPLE 7

A liquid dentifrice of the following composition was prepared in a conventional manner and examined for the factors.

| Ingredients | % by weight |
|---|---|
| Zirconosilicate | 20 |
| (specific surface area 20 m$^2$/g) | |
| Xanthan gum | 0.15 |
| Sodium polyacrylate | 0.15 |
| Propylene glycol | 2 |
| Sorbitol | 30 |
| Glycerin | 20 |
| Saccharin sodium | 0.1 |
| Flavor | 1.0 |
| Coloring agent (Brilliant Blue) | 0.001 |
| Decaglyceryl laurate | 1 |
| Sodium laurylsulfate | 1.5 |
| Sodium fluoride | 0.2 |
| Butyl p-hydroxybenzoate | 0.01 |
| Pure water | balance |
| | 100.0% |
| Viscosity | 60 poise |
| Yield value, fresh | 7 Pa |
| after @40° C./1 mth. | 7.5 Pa |
| Brush soaking time | 85 sec. |

-continued

| | |
|---|---|
| Flow | 5 |
| Dispersion stability | OK |
| Cleaning power | OK |
| Stringiness | 3 |
| Index of refraction | 1.44 |
| Overall evaluation | Exc. Passed |

EXAMPLE 8

A liquid dentifrice of the following composition was prepared in a conventional manner and examined for the factors.

| Ingredients | % by weight |
|---|---|
| Precipitated silica (specific surface area 40 m²/g) | 15 |
| Xanthan gum | 0.2 |
| Sodium polyacrylate | 0.2 |
| Propylene glycol | 2 |
| Sorbitol | 35 |
| Glycerin | 10 |
| Saccharin sodium | 0.1 |
| Flavor | 1.0 |
| Sodium chloride | 5.0 |
| β-glycyrrhetinic acid | 0.02 |
| Sodium laurylsulfate | 1.5 |
| Butyl p-hydroxybenzoate | 0.02 |
| Pure water | balance |
| | 100.0% |
| Viscosity | 55 poise |
| Yield value, fresh | 6 Pa |
| after @40° C./1 mth. | 6.3 Pa |
| Brush soaking time | 75 sec. |
| Flow | 5 |
| Dispersion stability | OK |
| Cleaning power | OK |
| Stringiness | 3 |
| Index of refraction | 1.44 |
| Overall evaluation | Exc. Passed |

EXAMPLE 9

A liquid dentifrice of the following composition was prepared in a conventional manner and examined for the factors.

| Ingredients | % by weight |
|---|---|
| Zirconosilicate (specific surface area 40 m²/g) | 30 |
| Sodium carboxymethyl cellulose | 0.2 |
| Carrageenan | 0.2 |
| Propylene glycol | 2 |
| Sorbitol | 35 |
| Saccharin sodium | 0.1 |
| Flavor | 1.0 |
| Sodium ascorbate | 0.02 |
| Sodium laurylsulfate | 1.5 |
| Sodium p-hydroxybenzoate | 0.3 |
| Pure water | balance |
| | 100.0% |
| Viscosity | 105 poise |
| Yield value, fresh | 32 Pa |
| after @40° C./1 mth. | 34 Pa |
| Brush soaking time | 115 sec. |
| Flow | 4 |
| Dispersion stability | OK |
| Cleaning power | OK |
| Stringiness | 3 |
| Index of refraction | 1.41 |
| Overall evaluation | Passed |

EXAMPLE 10

A liquid dentifrice of the following composition was prepared in a conventional manner and examined for the factors.

| Ingredients | % by weight |
|---|---|
| Zirconosilicate (specific surface area 40 m²/g) | 20 |
| Xanthan gum | 0.2 |
| Sodium polyacrylate | 0.3 |
| Propylene glycol | 2 |
| Sorbitol | 40 |
| Saccharin sodium | 0.1 |
| Flavor | 1.0 |
| Coloring agent (Brilliant Blue) | 0.001 |
| Sodium laurylsulfate | 1.5 |
| Isopropylmethylphenol | 0.05 |
| Sodium monofluorophosphate | 0.76 |
| Pure water | balance |
| | 100.0% |
| Viscosity | 89 poise |
| Yield value, fresh | 18 Pa |
| after @40° C./1 mth. | 19 Pa |
| Brush soaking time | 230 sec. |
| Flow | 5 |
| Dispersion stability | OK |
| Cleaning power | OK |
| Stringiness | 3 |
| Index of refraction | 1.43 |
| Overall evaluation | Exc. Passed |

COMPARATIVE EXAMPLE 1

A liquid dentifrice of the following composition was prepared in a conventional manner and examined for the factors.

| Ingredients | % by weight |
|---|---|
| Precipitated silica (specific surface area 40 m²/g) | 20 |
| Xanthan gum | 0.07 |
| Sodium polyacrylate | 0.08 |
| Propylene glycol | 2 |
| Sorbitol | 40 |
| Saccharin sodium | 0.1 |
| Flavor | 1.0 |
| Coloring agent (Brilliant Blue) | 0.001 |
| Sodium laurylsulfate | 1.5 |
| Pure water | balance |
| | 100.0% |
| Viscosity | 14.5 poise |
| Yield value, fresh | 2.8 Pa |
| after @40° C./1 mth. | 3 Pa |
| Brush soaking time | 9 sec. |
| Flow | 5 |
| Dispersion stability | NO |
| Cleaning power | OK |
| Stringiness | 3 |
| Index of refraction | 1.43 |
| Overall evaluation | Rejected |

COMPARATIVE EXAMPLE 2

A liquid dentifrice of the following composition was prepared in a conventional manner and examined for the factors.

| Ingredients | % by weight |
|---|---|
| Calcium carbonate (specific surface area 5 m²/g) | 45 |
| Sodium carboxymethyl cellulose | 0.4 |

-continued

| | |
|---|---|
| Carrageenan | 0.6 |
| Propylene glycol | 2 |
| Sorbitol | 25 |
| Saccharin sodium | 0.1 |
| Flavor | 1.0 |
| Sodium laurylsulfate | 1.5 |
| Pure water | balance |
| | 100.0% |
| Viscosity | 700 poise |
| Yield value, fresh | 73 Pa |
| after @40° C./1 mth. | 76 Pa |
| Brush soaking time | 1000 sec. |
| Flow | 1 |
| Dispersion stability | OK |
| Cleaning power | OK |
| Stringiness | 3 |
| Overall evaluation | Rejected |

COMPARATIVE EXAMPLE 3

A liquid dentifrice of the following composition was prepared in a conventional manner and examined for the factors.

| Ingredients | % by weight |
|---|---|
| Aluminosilicate | 30 |
| (specific surface area 80 m$^2$/g) | |
| Sodium polyacrylate | 0.2 |
| Carrageenan | 0.4 |
| Propylene glycol | 2 |
| Sorbitol | 25 |
| Glycerin | 25 |
| Saccharin sodium | 0.1 |
| Flavor | 1.0 |
| Sodium laurylsulfate | 1.5 |
| Methyl p-hydroxybenzoate | 0.02 |
| Pure water | balance |
| | 100.0% |
| Viscosity | 300 poise |
| Yield value, fresh | 60 Pa |
| after @40° C./1 mth. | 63 Pa |
| Brush soaking time | 1000 sec. |
| Flow | 1 |
| Dispersion stability | OK |
| Cleaning power | OK |
| Stringiness | 2 |
| Index of refraction | 1.44 |
| Overall evaluation | Rejected |

COMPARATIVE EXAMPLE 4

A liquid dentifrice of the following composition was prepared in a conventional manner and examined for the factors.

| Ingredients | % by weight |
|---|---|
| Precipitated silica | 30 |
| (specific surface area 200 m$^2$/g) | |
| Xanthan gum | 0.6 |
| Carrageenan | 0.6 |
| Propylene glycol | 2 |
| Sorbitol | 20 |
| Saccharin sodium | 0.15 |
| Flavor | 1.0 |
| Sodium laurylsulfate | 2 |
| Sodium fluoride | 0.2 |
| Pure water | balance |
| | 100.0% |
| Viscosity | 850 poise |
| Yield value, fresh | 72 Pa |
| after @40° C./1 mth. | 80 Pa |
| Brush soaking time | 1000 sec. |
| Flow | 1 |
| Dispersion stability | OK |
| Cleaning power | OK |
| Stringiness | 1 |
| Overall evaluation | Rejected |

COMPARATIVE EXAMPLE 5

A liquid dentifrice of the following composition was prepared in a conventional manner and examined for the factors.

| Ingredients | % by weight |
|---|---|
| Calcium hydrogen phosphate | 3 |
| (specific surface area 6 m$^2$/g) | |
| Sodium polyacrylate | 0.4 |
| Sodium carboxymethyl cellulose | 0.3 |
| Propylene glycol | 1.5 |
| Sorbitol | 20 |
| Glycerin | 30 |
| Saccharin sodium | 0.1 |
| Flavor | 1.0 |
| Sodium laurylsulfate | 1.5 |
| Pure water | balance |
| | 100.0% |
| Viscosity | 75 poise |
| Yield value, fresh | 4 Pa |
| after @40° C./1 mth. | 4 Pa |
| Brush soaking time | 65 sec. |
| Flow | 4 |
| Dispersion stability | OK |
| Cleaning power | NO |
| Stringiness | 3 |
| Overall evaluation | Rejected |

COMPARATIVE EXAMPLE 6

A liquid dentifrice of the following composition was prepared in a conventional manner and examined for the factors.

| Ingredients | % by weight |
|---|---|
| Aluminum hydroxide | 20 |
| (specific surface area 3.3 m$^2$/g) | |
| Xanthane gum | 0.5 |
| Propylene glycol | 1.5 |
| Sorbitol | 40 |
| Glycerin | 8.5 |
| Saccharin sodium | 0.1 |
| Flavor | 1.0 |
| Sodium laurylsulfate | 1.5 |
| Pure water | balance |
| | 100.0% |
| Viscosity | 40 poise |
| Yield value, fresh | 6 Pa |
| after @40° C./1 mth. | 6.2 Pa |
| Brush soaking time | 90 sec. |
| Flow | 5 |
| Dispersion stability | OK |
| Cleaning power | OK |
| Stringiness | 1 |
| Overall evaluation | Rejected |

COMPARATIVE EXAMPLE 7

A liquid dentifrice of the following composition was prepared in a conventional manner and examined for the factors.

| Ingredients | % by weight |
|---|---|
| Calcium hydrogen phosphate (specific surface area 6 m$^2$/g) | 25 |
| Sodium polyacrylate | 0.4 |
| Propylene glycol | 2 |
| Sorbitol | 30 |
| Glycerin | 20 |
| Saccharin sodium | 0.1 |
| Flavor | 1.0 |
| Sodium laurylsulfate | 1.5 |
| Sodium fluoride | 0.2 |
| Pure water | balance |
| | 100.0% |
| Viscosity | 45 poise |
| Yield value, fresh | 6.5 Pa |
| after @40° C./1 mth. | 6.5 Pa |
| Brush soaking time | 130 sec. |
| Flow | 4 |
| Dispersion stability | NO |
| Cleaning power | OK |
| Stringiness | 2 |
| Overall evaluation | Rejected |

Although some preferred embodiments have been described, many modifications and variations may be made thereto in the light of the above teachings. It is therefore to be understood that within the scope of the appended claims, the invention may be practiced otherwise than as specifically described.

We claim:

1. A pump dispenser or squeeze bottle container liquid dentifrice composition comprising an aqueous medium containing a binder in the form of xanthan gum and a humectant, and 5 to 40% by weight of the composition being a silica abrasive having a specific surface area of 5 to 100 m$^2$/g as measured by BET method, said liquid dentifrice composition having a viscosity of 20 to 180 poise at 25° C. and a yield value of 1 to 60 Pascal at 25° C., said liquid dentifrice composition being:
   a) dispensed as a fluid, by extrusion,
   b) sufficiently viscous to remain on top of, and not quickly soak through, the bristles of the toothbrush,
   c) easily rinsed away from a toothbrush, and,
   d) after rinsing, leaving no significant deposits adhered to the bristles, said liquid dentifrice having improved stringiness, and being neither a gel dentifrice nor a toothpaste, said abrasive kept stably dispersed without settling down, and with minimized lowering of fluidity, with a binder in an amount of 0.05 to 2% by weight, and 10 to 80% by weight of a humectant in an amount effective to achieve the viscosity and yield value in the specified ranges.

2. The composition of claim 1, wherein the silica abrasive and the aqueous medium have an approximately equal index of refraction so that the composition is transparent.

3. A liquid dentifrice composition comprising an aqueous medium containing a binder in the form of a mixture of xanthan gum and a polyacrylic acid salt in a weight ratio of from 3:1 to 1:5 and a humectant, and 5 to 40% by weight of the composition being a silica abrasive having a specific surface area of 5 to 100 m$^2$/g as measured by BET method, said liquid dentifrice composition having a viscosity of 20 to 180 poise at 25° C. and a yield value of 1 to 60 Pascal at 25° C., said liquid dentifrice composition being:
   a) dispensed as a fluid, by extrusion,
   b) sufficiently viscous to remain on top of, and not quickly soak through, the bristles of the toothbrush,
   c) easily rinsed away from a toothbrush, and,
   d) easily rinsing, leaving no significant deposits adhered to the bristles, said liquid dentifrice having improved stringiness, and being neither a gel dentifrice nor a toothpaste, said abrasive kept stably dispersed without settling down, and with minimized lowering of fluidity, with a binder in an amount of 0.05 to 2% by weight, and 10 to 80% by weight of a humectant in an amount effective to achieve the viscosity and yield value in the specified ranges.

4. The composition of claim 3, wherein the silica abrasive and the aqueous medium have an approximately equal index of refraction so that the composition is transparent.

5. The composition of claim 1, wherein said abrasive has a specific surface area of 5 to 30 m$^2$/g.

6. The composition of claim 1, wherein said abrasive has a mean particle size of about 1 to 20 μm.

7. The composition of claim 1, wherein said abrasive is present in an amount of 10 to 25% by weight of the composition.

8. The composition of claim 1, wherein said liquid dentifrice composition has a viscosity of 30 to 70 poise at 25° C. and a yield value of 5 to 50 Pascal.

9. The composition of claim 1, wherein said liquid dentifrice composition has a yield value of 5 to 20 Pascal.

10. The composition of claim 8, wherein said liquid dentifrice composition has a yield value of 5 to 20 Pascal.

11. The composition of claim 1, wherein said binder is present in an amount of 0.1 to 2% by weight.

12. The composition of claim 1, wherein said humectant is selected from the group consisting of glycerine, sorbitol, propylene glycol, ethylene glycol, 1,3-butylene glycol, polyethylene glycol, polypropylene glycol, xylitol, maltitol, lactitol and mixtures thereof.

13. The composition of claim 3, wherein the mixture of xanthan gum and polyacrylic acid salt is in a weight ratio of from 3:2 to 1:2.

14. The composition of claim 1, wherein the binder is present in an amount of 0.3 to 0.5% by weight of the total weight of the composition.

15. The composition of claim 1, wherein the humectant is present in an amount of 20 to 60% by weight of the total weight of the composition.

16. The composition of claim 3, wherein said abrasive has a specific surface area of 5 to 30 m$^2$/g.

17. The composition of claim 3, wherein said abrasive has a mean particle size of about 1 to 20 μm.

18. The composition of claim 3, wherein said abrasive is present in an amount of 10 to 25% by weight of the composition.

19. The composition of claim 3, wherein said liquid dentifrice composition has a viscosity of 30 to 70 poise at 25° C. and a yield value of 5 to 50 Pascal.

20. The composition of claim 3, wherein said liquid dentifrice composition has a yield value of 5 to 20 Pascal.

21. The composition of claim 20, wherein said liquid dentifrice composition has a yield value of 5 to 20 Pascal.

22. The composition of claim 3, wherein said binder is present in an amount of 0.1 to 2% by weight.

23. The composition of claim 3, wherein said humectant is selected from the group consisting of glycerine, sorbitol, propylene glycol, ethylene glycol, 1,3-butylene glycol, polyethylene glycol, polypropylene glycol, xylitol, maltitol, lactitol and mixtures thereof.

24. The composition of claim 3, wherein the binder is present in an amount of 0.3 to 0.5% by weight of the total weight of the composition.

25. The composition of claim 3, wherein the humectant is present in an amount of 20 to 60% by weight of the total weight of the composition.

* * * * *